US008241882B2

(12) United States Patent
Tanisho et al.

(10) Patent No.: US 8,241,882 B2
(45) Date of Patent: Aug. 14, 2012

(54) **HYDROGEN-PRODUCING BACTERIUM, *CLOSTRIDIUM PERFRINGENS***

(75) Inventors: Shigeharu Tanisho, Chigasaki (JP); Hiroki Nishiyama, Yokohama (JP)

(73) Assignee: National University Corporation Yokohama National University, Kanagawa (JP)

( * ) Notice: Subject to any disclaimer, the term of this patent is extended or adjusted under 35 U.S.C. 154(b) by 117 days.

(21) Appl. No.: 12/530,712

(22) PCT Filed: Mar. 12, 2008

(86) PCT No.: PCT/JP2008/054485
§ 371 (c)(1), (2), (4) Date: Feb. 10, 2010

(87) PCT Pub. No.: WO2008/111608
PCT Pub. Date: Sep. 18, 2008

(65) Prior Publication Data

US 2010/0233776 A1 Sep. 16, 2010

(30) Foreign Application Priority Data

Mar. 14, 2007 (JP) ................................ 2007-064932

(51) Int. Cl.

| | |
|---|---|
| ***C12P 3/00*** | (2006.01) |
| ***C12N 9/00*** | (2006.01) |
| ***C12N 1/20*** | (2006.01) |
| ***C12N 15/00*** | (2006.01) |
| ***C07H 21/04*** | (2006.01) |

(52) U.S. Cl. ..................... 435/168; 435/183; 435/252.3; 435/252.7; 435/320.1; 536/23.2

(58) Field of Classification Search ........................ None
See application file for complete search history.

(56) References Cited

FOREIGN PATENT DOCUMENTS

| | | |
|---|---|---|
| JP | 2001-157595 | 6/2001 |
| JP | 2006-180782 | 7/2006 |

OTHER PUBLICATIONS

Morimoto et al. FEMS Microbiol Lett. May 15, 2005;246(2):229-34.*

Schroder et al., "Glucose fermentation to acetate, CO2 and H2 in the anaerobic hyperthermophilic eubacterium *Thermotoga maritima*: involvement of the Embden-Meyerhof pathway", Archives of Microbiology 161, p. 460-470, (1994).

Taguchi, F. et al., Isolation of a hydrogen-producing bacterium, *Clostridium beijerinckii* strain AM21B, from termites, Can. J. Microbiol., 1993, vol. 39, p. 726-730.

Evvyernie, D. et al., Identification and Characterization of *Clostridium paraputrificum* M-21, a Chitinolytic, Mesophilic and Hydrogen-Producing Bacterium, Journal of Bioscience and Bioengineering, 2000, vol. 89, No. 6, p. 596-601.

Heyndrickx, M. et al., Hydrogen Gas Production from Continuous Fermentation of Glucose in a Minimal Medium with *Clostridium butyricum* LMG 1213tl., System. Appl. Microbiol., 1986, vol. 8, p. 239-244.

Taguchi, F. et al., Microbial conversion of arabinose and xylose to hydrogen by a newly isolated *Clostridium* sp. No. 2., Can J. Microbiol., 1994, vol. 40, p. 228-233.

Japanese Patent Office, Search Report and Written Opinion in International Patent Application No. PCT/JP2008/054485 dated Apr. 15, 2008.

Kaji, M. et al., The hydA gene encoding the H2-evolving hydrogenase of *Clostridium perfringens*: molecular characterization and expression of the gene, FEMS Microbiology Letters, 1999, vol. 181, No. 2, p. 329-336.

*Clostridium absonum*, 1976, vol. 85, No. 5/6, p. 502-510.

Sacks, L.E. and Olson, A.C., Growth of *Clostridium perfringens* Strains on Alpha-galactosides., Journal of Food Science, 1979, vol. 44, No. 6, p. 1756-1764, abstract.

Nche, P.F. et al., Gas production by *Clostridium perfringens* as a measure of the fermentability of carbohydrates and processed cereal-legume foods., Food Microbiology, 1994, vol. 11, No. 1, p. 21-29, abstract, table 3,4.

* cited by examiner

*Primary Examiner* — Christian Fronda
(74) *Attorney, Agent, or Firm* — Wood, Herron & Evans, LLP

(57) ABSTRACT

The present invention aims to provide a hydrogen-producing bacterium, which excels in hydrogen yield and hydrogen production rate, and is usable for industrial hydrogen production from biomass as a production source. That is, it is intended to provide a bacterium belonging to the genus *Clostridium* which has a property of producing hydrogen at a rate of 60 mmol or more per hour per liter of a culture liquid which contains glucose as a substrate, by batch cultivation in a YNU anaerobic culture medium at 47° C. and pH 6.0, and a hydrogen production method comprising the use of the bacterium belonging to the genus *Clostridium.*

6 Claims, 2 Drawing Sheets

SEQUENCE LISTING

```
<160> NUMBER OF SEQ ID NOS: 1

<210> SEQ ID NO 1
<211> LENGTH: 975
<212> TYPE: DNA
<213> ORGANISM: Clostridium perfringens
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (918)..(918)
<223> OTHER INFORMATION: n is a, c, g, or t
<220> FEATURE:
<221> NAME/KEY: misc_feature
<222> LOCATION: (924)..(924)
<223> OTHER INFORMATION: n is a, c, g, or t
<220> FEATURE:
<221> NAME/KEY: misc_feature
<222> LOCATION: (939)..(939)
<223> OTHER INFORMATION: n is a, c, g, or t
<220> FEATURE:
<221> NAME/KEY: misc_feature
<222> LOCATION: (944)..(945)
<223> OTHER INFORMATION: n is a, c, g, or t
<220> FEATURE:
<221> NAME/KEY: misc_feature
<222> LOCATION: (948)..(948)
<223> OTHER INFORMATION: n is a, c, g, or t
<220> FEATURE:
<221> NAME/KEY: misc_feature
<222> LOCATION: (954)..(954)
<223> OTHER INFORMATION: n is a, c, g, or t
<220> FEATURE:
<221> NAME/KEY: misc_feature
<222> LOCATION: (961)..(961)
<223> OTHER INFORMATION: n is a, c, g, or t
<220> FEATURE:
<221> NAME/KEY: misc_feature
<222> LOCATION: (970)..(970)
<223> OTHER INFORMATION: n is a, c, g, or t

<400> SEQUENCE: 1

ccccnatcgc tgaccctacc ttcggccgct gcctccttgc ggttagctca cggacttcgg      60

gtattgccaa ctctcatggt gtgacgggcg gtgtgtacaa gacccgggaa cgtattcacc     120

gcgacattct gattcgcgat tactagtaac tccagcttca tgtaggcgag tttcagccta     180

caatccgaac tgagactggt tttaaagttt ggctccacct cacggtattg catctctctg     240

taccagccat tgtagcacgt gtgtagccct acacataagg ggcatgatga tttgacgtca     300

tccccacctt cctcctggtt aacccaggca gtctcgctag agtcctcaac ttaatggtag     360

taactaacga caagggttgc gctcgttgcg ggacttaacc caacatctca cgacacgagc     420

tgacgacaac catgcaccac ctgtcacctt gtccccgaag ggatttcctc gattaagagt     480

aatgcaaggg atgtcaagtg taggtaaggt tcttcgcgtt gcttcgaatt aaaccacatg     540

ctccgctact tgtgcgggtc cccgtcaatt cctttgagtt ttaatcttgc gaccgtactc     600

cccaggcgga atacttaatg cgttagcggc ggcacggagg tgttgaaacc cccacaccta     660
```

-continued

```
gtattcatcg tttacggcgt ggactaccag ggtatctaat cctgtttgct ccccacgctt    720

tcgagcctca gcgtcagtta cagtccagag agtcgccttc gccactggtg ttcttcctaa    780

tctctacgca tttcaccgct acactaggaa ttccactctc ctctcctgca ctctagataa    840

ccagtttgga atgcagcacc caagttgagc ccgggtattt cacatcccac ttaatcatcc    900

gcctacgctc cctttacncc cagnaaatcc ggataacgnt cgcnnccnac gtantaccgc    960

ngctgctggn acgta                                                     975
```

HYDROGEN-PRODUCING BACTERIUM, *CLOSTRIDIUM PERFRINGENS*

TECHNICAL FIELD

The present invention relates to a novel hydrogen-producing bacterium belonging to the genus *Clostridium*, and a hydrogen production method using the hydrogen-producing bacterium.

BACKGROUND ART

In recent years, hydrogen fuel has been attracting attention as a substitute energy for fossil fuels such as petroleum, because it is a renewable and clean energy which, unlike fossil fuels, emits little carbon dioxide and other environmental pollutants by burning. For this reason, more efficient hydrogen production methods have been enthusiastically studied all over the world.

Hydrogen can be produced from various production sources, although it is preferably produced from biomass as a production source from a viewpoint of recycling. Such hydrogen production methods from biomass mainly involve thermochemical methods and biological methods with use of bacteria. Of these, biological methods are preferred. The reason is that thermochemical methods such as hot gasification are cost-consuming since biomass normally contains lots of moisture because of its nature as an energy product of organic wastes, sugar cane, etc.

Bacteria for use in hydrogen production from biomass can be largely categorized in photosynthetic bacteria and fermentative bacteria. The photosynthetic bacteria are capable of complete decomposition of organic matters contained in biomass into water and carbonic gas by using light energy. However, the drawback is that light energy can be used only during the day and becomes insufficient in the morning and the evening. On the other hand, the fermentative bacteria are capable of producing hydrogen even in a sealed container, and are suitable for hydrogen production from biomass having high moisture contents such as raw garbage and waste molasses. In addition, the hydrogen production rate of fermentative bacteria is higher than that of photosynthetic bacteria. For these reasons, hydrogen production methods with use of fermentative bacteria have been mainly employed in the field of industry.

Anaerobic fermentative bacteria for use in the hydrogen production from biomass include bacteria belonging to the genus *Clostridium* such as *Clostridium butyricum* and bacteria belonging to the genus *Enterobacter* such as *Enterobacter aerogenes* (for example, refer to Non-patent Document 1). As a hydrogen production method from biomass with use of a bacterium belonging to the genus *Clostridium*, for example, there is disclosed (1) a method for production of hydrogen by generating hydrogen from an organic material, comprising: a charging step for charging the organic material; a microorganism-charging step for charging a microorganism belonging to the genus *Clostridium*; a reaction step for reacting the microorganism with the organic material to produce hydrogen; and a stirring step, during the reaction step, for stirring the organic material and the microorganism in order to promote the reaction and decomposition (for example, refer to Patent Document 1). In addition, as a hydrogen production method from biomass with use of a bacterium belonging to the genus *Enterobacter*, for example, there is disclosed (2) a method for producing hydrogen and ethanol from a raw material liquid which contains a biodiesel waste liquid obtained through demethylesterification of a methylesterified-oil and fat wherein the method comprises a fermentation step for fermenting with a bacterium belonging to the genus *Enterobacter* at least in the presence of a carrier whose surface is capable of immobilizing microorganisms (for example, refer to Patent Document 2).

Bacteria belonging to the genus *Clostridium* and bacteria belonging to the genus *Enterobacter* are normally hydrogen-producing bacteria which produce hydrogen at 30 to 38° C. In contrast, there exist high-temperature hydrogen-producing bacteria which produce hydrogen at 65 to 80° C., and high-temperature hydrogen fermentation methods using the same. As compared to the hydrogen production methods using bacteria belonging to the genus *Clostridium* or the like, the high-temperature hydrogen fermentation methods are advantageous in the points of improved hydrogen yield and easy prevention of the substrate contamination caused by various germs. For example, *Thermotoga maritima* has achieved a theoretically maximum hydrogen yield of 4 mol/mol-glucose by batch cultivation at 80° C. (for example, refer to Non-patent Document 2). Such a high hydrogen yield at high temperature can be attributed to the suppression against metabolism of undesirable by-products such as lactic acid.

Non-patent Document 1: de Vrije and Classen (2003) "Dark hydrogen fermentations" in Bio-methane and Bio-hydrogen, p103 to 121

Patent Document 1: Japanese Unexamined Patent Application, First Publication No. 2001-157595

Patent Document 2: Japanese Unexamined Patent Application, First Publication No. 2006-180782

Non-patent Document 2: Schroder et al. (1994) Archives of microbiology 161: p460 to 470

DISCLOSURE OF INVENTION

Biomass such as a food waste etc. contains various substances which inhibit hydrogen-producing bacteria from producing hydrogen. Therefore, hydrogen-producing bacterium for use in hydrogen production from biomass desirably excel in hydrogen yield and hydrogen production rate.

However, known bacteria belonging to the genus *Enterobacter* and the like which produce hydrogen at 30 to 38° C. are not sufficient in hydrogen yield and hydrogen production rate, and it is very difficult to use such bacteria for industrial hydrogen production from biomass as a production source.

On the other hand, high-temperature hydrogen-producing bacteria which produce hydrogen at 65 to 80° C. are very inferior in hydrogen production rate although they excel in hydrogen yield. Therefore, these bacteria are not suitable for industrial use, either. For example, the hydrogen production rate of *Thermotoga maritima* is no more than 10 mmol/L·h per hour per liter of a batch culture liquid at 80° C. (for example, refer to Non-patent Document 2). Such a low hydrogen production rate at high temperature can be attributed to a low cell density of the bacterium.

The present invention is intended to provide a hydrogen-producing bacterium, which excels in hydrogen yield and hydrogen production rate, and is usable for industrial hydrogen production from biomass as a production source.

In addition, the present invention is also intended to provide a hydrogen production method which uses the hydrogen-producing bacterium.

The inventors of the present invention have conducted intensive studies to solve the abovementioned problems. As a result, they have come to the opinion that both the hydrogen yield and the hydrogen production rate can be improved by producing hydrogen at an intermediate temperature between 30 to 38° C. and 65 to 80° C., and have singled out a hydrogen-producing bacterium capable of satisfactorily producing hydrogen at about 50° C. This has led to the completion of the present invention.

That is, the present invention relates to the following aspects.

(1) A bacterium belonging to the genus *Clostridium* which has a property of producing hydrogen at a rate of 60 mmol or more per hour per liter of a culture liquid which contains glucose as a substrate, by cultivation in a YNU anaerobic culture medium at 47° C. and pH 6.0.

(2) A bacterium belonging to the genus *Clostridium* according to (1), wherein the bacterium is *Clostridium perfringens.*

(3) A bacterium belonging to the genus *Clostridium* according to either one of (1) and (2), wherein the optimum temperature for hydrogen production is 47 to 50° C.

(4) A bacterium belonging to the genus *Clostridium* according to any one of (1) through (3), wherein the optimum temperature for cell growth is 44 to 47° C.

(5) A bacterium belonging to the genus *Clostridium* according to any one of (1) through (4), wherein the bacterium has a raffinose-decomposing ability.

(6) A bacterium belonging to the genus *Clostridium* according to any one of (1) through (5), wherein the bacterial strain is *Clostridium perfringens* HN001 (NITE BP-318).

(7) A hydrogen production method comprising the use of the bacterium belonging to genus *Clostridium* according to any one of (1) through (6).

In the hydrogen production method according to (7), the bacterium belonging to genus *Clostridium* is preferably cultured at 47 to 50° C. In addition, the pH of the culture liquid used therein is preferably 5.8 to 6.5, and more preferably 6.0 to 6.2.

(8) Use of the bacterium belonging to genus *Clostridium* according to any one of (1) through (6) for the production of hydrogen.

The bacterium belonging to the genus *Clostridium* of the present invention is a hydrogen-producing bacterium which is not inferior in hydrogen yield and quite excels in hydrogen production rate. Accordingly, the use of the bacterium belonging to the genus *Clostridium* of the present invention and the hydrogen production method of the present invention are capable of hydrogen production with higher efficiency than ever before, even from biomass as a production source. In addition, the present invention is capable of maintaining the temperature with less energy as compared to high-temperature hydrogen fermentation methods which require a large amount of energy for maintaining the temperature, and thus is preferable in terms of economy.

BRIEF DESCRIPTION OF THE DRAWINGS

FIG. 1A shows the measurement results of timewise changes in the bacterial dry weight at respective temperatures, wherein the Y axis shows the bacterial dry weight per liter of a culture liquid (g/L), and the X axis shows the cultivation time (h). The solid diamond shows the result at 32° C., the open square shows the result at 37° C., the open triangle shows the result at 41° C., the mark x shows the result at 44° C., the solid circle shows the result at 47° C., and the solid triangle shows the result at 50° C.

FIG. 1B particularly shows the calculation results of the maximum growth rates at respective temperatures.

BEST MODE FOR CARRYING OUT THE INVENTION

Figure 1A:
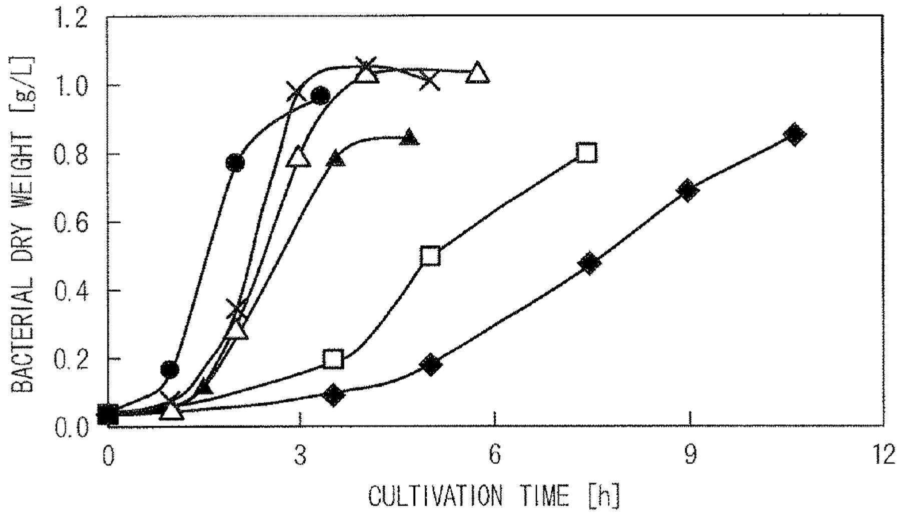
FIG. 1A shows the effect of the temperature on the growth of *Clostridium perfringens* strain HN001.

The YNU anaerobic culture medium of the present invention consists of a composition shown in Table 1, and is suitable for cultivation of anaerobes. The respective reagents are commercially available in usual markets. For example, the followings can be used: casein peptone manufactured by Nihon Pharmaceutical, Dried Yeast Extract-S manufactured by Wako Pure Chemical, L-cystein hydrochloride monohydrate manufactured by Junsei Chemical, mercaptoacetic acid manufactured by Junsei Chemical, and D(+) glucose manufactured by Wako Pure Chemical. The glucose concentration can be appropriately determined according to the cultivation condition or the like. In addition, casamino acid may be used instead of casein peptone.

TABLE 1

| Composition of YNU anaerobic culture medium (g/L) | |
|---|---|
| Casein peptone | 25.0 |
| Dried Yeast Extract-S | 22.0 |
| L-cystein hydrochloride monohydrate | 0.3 |
| Mercaptoacetic acid | 0.3 |
| D(+) glucose | 15.0 |

The bacteria belonging to the genus *Clostridium* of the present invention, in particular *Clostridium perfringens*, are hydrogen-producing bacteria which have a property of producing hydrogen at a rate of 60 mmol or more per hour per liter of a culture liquid which contains glucose as a substrate, by batch cultivation in a YNU anaerobic culture medium at 47° C. and pH 6.0. The reason is that the hydrogen production at about 50° C. leads to a higher reaction rate of the hydrogen fermentation than at 30 to 38° C., and thus can be considered to contribute to more efficient hydrogen production. Another reason is that a hydrogen-producing bacterium exhibiting excellent hydrogen productivity which achieves a hydrogen production rate of 60 mmol or more per hour per liter of a culture liquid, is capable of producing a larger amount of hydrogen than ever before, even from biomass containing a wide variety of substances as a production source. The hydrogen productivity is not specifically limited as long as it achieves a hydrogen production rate of 60 mmol or more, more preferably 80 mmol or more, and particularly preferably 100 mmol or more, per hour per liter of a culture liquid.

The bacterium belonging to the genus *Clostridium* of the present invention can be acquired by the following manner, for example. First, bacterial strains are isolated from nature-derived samples. From these bacterial strains is selected a bacterial strain exhibiting a hydrogen productivity which achieves a hydrogen production rate of 60 mmol or more per hour per liter of a culture liquid at about 50° C., by which the bacterium belonging to the genus *Clostridium* of the present invention can be acquired.

Hereunder is a more detailed description.

1. Acquisition of Bacterial Strain

Samples including liquids and sludges collected from sewage and the like were inoculated in an ABCM semisolid stab culture medium having a composition shown in Table 2 (Eiken Chemical), and then incubated in a thermostat at 50° C., followed by selection of samples exhibiting active gas productions. The thus selected samples were applied to an ABCM agar medium (Eiken Chemical), and subjected to anaerobic cultivation at 50° C. to thereby obtain colonies. Further, from these colonies, bacteria were aseptically taken and subjected to anaerobic cultivation in the same manner to thereby acquire purely isolated bacterial strains. The purely isolated bacterial strains were inoculated in the YNU anaerobic culture medium and further incubated in the thermostat at 50° C. to thereby select samples exhibiting active gas productions. From the thus selected bacterial strains, bacterial strains exhibiting hydrogen productivities which achieved hydrogen production rates of 60 mmol or more per hour per liter of the culture liquid were selected. Of these, one strain was named HN001 and the hydrogen productivity thereof was examined more in detail. The hydrogen production rate was measured by the method of Example 1 that will be described later.

TABLE 2

| Composition of ABCM semisolid medium (g/L) | |
|---|---|
| Plant extract | 2.0 |
| Yeast extract | 5.0 |
| Meat extract | 3.0 |
| Peptone | 10.0 |
| Tryptone | 10.0 |
| Soypeptone | 3.0 |
| Soluble starch | 5.0 |
| Glucose | 3.0 |
| Sodium chloride | 2.0 |
| Dipotassium phosphate | 2.5 |
| L-cysteine hydrochloride | 0.3 |
| Sodium thioglycolate | 0.3 |
| Hemin | 0.005 |
| Agar | 2.0 |

2. Identification of Strain 1-1N001 and its Biochemical Character

In order to investigate the genetic property of the strain HN001, the 16S rDNA sequence of the strain HN001 was identified by a usual method. The 16S rDNA sequence is shown in SEQ ID: 1 in the sequence listing. This nucleotide sequence was subjected to the homology search on the international nucleotide sequence database (GenBank/DDJ/EMBL), the result of which showed a 98% homology with the nucleotide sequence of *Clostridium perfringens* ATCC 13124. Accordingly, the strain HN001 assumably belongs to *Clostridium perfringens.*

Furthermore, the biochemical character of the strain HN001 was investigated using the identification kit for strict anaerobes, API20A system (manufactured by bioMerieux S.A., imported and distributed by bioMerieux Japan) according to the instruction of the manufacturer. Specifically, a bacterial suspension of the strain HN001 was dispensed in tubes containing respective substrates, and anaerobically incubated for 24 hours. Then, based on the color change of the respective tubes, sugar-decomposing abilities and the like of the strain HN001 were determined by using the APILAB software (manufactured by bioMerieux S.A.).

TABLE 3

| | Substrate | | | | | | | | | | | |
|---|---|---|---|---|---|---|---|---|---|---|---|---|
| Bacteria | MD | URE | GLU | MAN | LAC | SAC | MAL | SAL | XYL | ARA | GEL | ESC |
| HN001 | 0 | 0 | 99 | 0 | 0 | 99 | 99 | 0 | 0 | 0 | 40 | 20 |
| *C. perfringens* | 0 | 0 | 99 | 0 | 88 | 91 | 99 | 1 | 0 | 0 | 99 | 1 |
| *Acti. viscosus* | 0 | 0 | 99 | 0 | 64 | 99 | 99 | 21 | 0 | 0 | 14 | 0 |

| | Substrate | | | | | | | |
|---|---|---|---|---|---|---|---|---|
| | GLY | CEL | MNE | MLZ | RAF | SOR | RHA | TRE |
| HN001 | 75 | 0 | 99 | 0 | 75 | 0 | 0 | 0 |
| *C. perfringens* | 79 | 4 | 99 | 0 | 16 | 16 | 0 | 75 |
| *Acti. viscosus* | 62 | 21 | 96 | 0 | 94 | 0 | 0 | 7 |

Table 3 is a summary of the analysis results by the APILAB software from five times independent experiments using the API20A system. The table also shows the expected measurement results of respective bacterial strains. The top lines in the table show the substrate contained in each tube. IND represents tryptophane, URE represents urea, GLU represents glucose, MAN represents mannite, LAC represents lactose, SAC represents sucrose, MAL represents maltose, SAL represents salicin, XYL represents xylose, ARA represents arabinose, GEL represents gelatin, ESC represents esculin ferric citrate, GLY represents glycerin, CEL represents cellobiose, MNE represents mannose, MLZ represents melezitose, RAF represents raffinose, SOR represents sorbitol, RHA represents rhamnose, and TRE represents trehalose.

As a result, the strain HN001 exhibited a glucose-decomposing ability, a sucrose-decomposing ability, a maltose-decomposing ability, and a mannose-decomposing ability, like *Clostridium perfringens*. On the other hand, unlike the known *Clostridium perfringens*, the strain HN001 exhibited a raffinose-decomposing ability while exhibiting neither lactose-decomposing ability nor trehalose-decomposing ability. In the determination by the APILAB software, the strain HN001 was concluded to be closer to *Actinomyces viscosus* than to *Clostridium perfringens.*

From its genetic property, the strain HN001 was confirmed to be a bacterium belonging to *Clostridium perfringens*. In addition, from the fact that the homology was 98%, and no known bacterium having a complete homology was found, and the biochemical character exhibited a raffinose-decomposing ability while exhibiting neither lactose-decomposing ability nor trehalose-decomposing ability, it is apparent that the strain HN001 has different properties to those of known bacterial strains.

Therefore, the applicants deposited the strain HN001 with the National Institute of Technology and Evaluation, Patent Microorganisms Depositary (2-5-8 Kazusakamatari, Kisarazu-shi, Chiba, #292-0818, Japan) as a national deposit (accession number: NITE P-318 original deposit) on Feb. 23, 2007. Furthermore, the applicants made a request for transfer to the international deposit under the Budapest Treaty, to the concerned international depositary authority on Mar. 3, 2008, and a receipt in respect of the original deposit (accession number of NITE BP-318) was issued on Mar. 7, 2008, 3. Optimum Temperature for Growth In order to investigate the effect of temperature on the growth of *Clostridium perfringens* strain HN001, cultivation was carried out at respective temperatures of 32, 37, 41, 44, 47, and 50° C.

Specifically, first, *Clostridium perfringens* strain HN001 was inoculated in a test tube containing an ABCM semisolid stab culture medium at pH 6.0, and was subjected to anaerobic cultivation at 30° C. for 16 hours as a preparation of a pre-culture liquid. The pre-culture liquid was added at 8 mL each to 350 mL of the YNU anaerobic culture medium at pH 6.0, followed by cultivation under the respective temperatures, and observation of the timewise change regarding the bacterial amount in the culture liquid. The cultivation was carried out at a stirring speed of 30 rpm. In addition, the bacterial amount in the culture liquid was measured by the following manner: each culture liquid was centrifuged, the bacterial matter was collected in a form of precipitate, and the dry weight of the precipitate was measured.

Figure 1B:
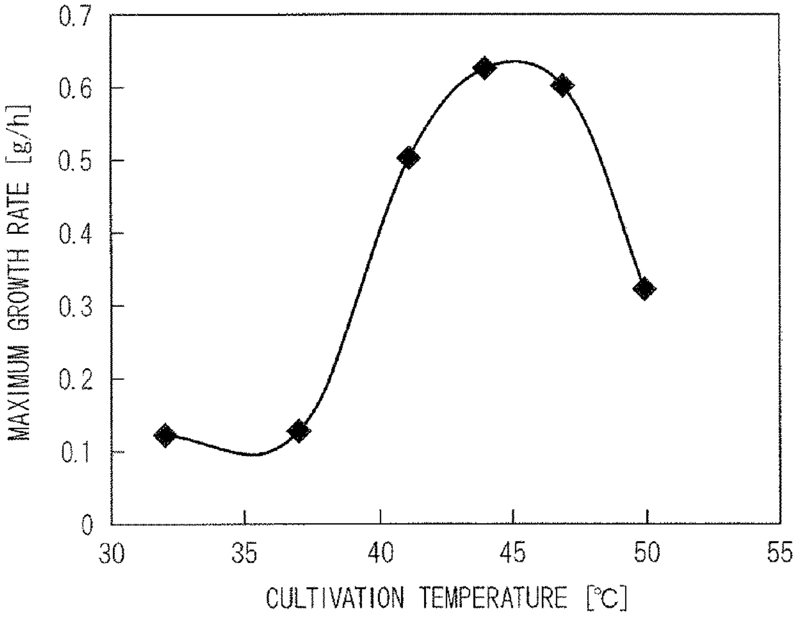
FIG. 1B shows the effect of the temperature on the growth of *Clostridium perfringens* strain HN001.

FIG. 1 shows the effect of the temperature on the growth of *Clostridium perfringens* strain HN001. FIG. 1A shows the measurement results of timewise changes in the bacterial dry weight at the respective temperatures, wherein the Y axis shows the bacterial dry weight per liter of the culture liquid (g/L), and the X axis shows the cultivation time (h). The solid diamond shows the result at 32° C., the open square shows the result at 37° C., the open triangle shows the result at 41° C., the mark x shows the result at 44° C., the solid circle shows the result at 47° C., and the solid triangle shows the result at 50° C. FIG. 1B shows the calculation results of the maximum growth rates at the respective temperatures obtained based on the measurement results. From these results it is apparent that the preferable growth temperature of *Clostridium perfringens* strain HN001 is 44 to 47° C.

The growth of *Clostridium perfringens* strain HN001 was confirmed at 51° C., but not at 53° C. From these results, *Clostridium perfringens* strain HN001 was found to be growable at 32° C. to 51° C.

4. Measurement of Hydrogen Productivity

*Clostridium perfringens* strain HN001 was inoculated in a test tube containing 16 mL of the ABCM semisolid stab culture medium, and was subjected to anaerobic cultivation at 30° C. for 16 hours. Then, in order to acclimatize to high temperatures, the test tube was anaerobically incubated at 45° C. for 30 minutes for use as a pre-culture liquid. The pre-culture liquid was inoculated respectively in the YNU anaerobic culture medium at pH 6.0, or a YNU anaerobic culture medium at pH 6.0 which had been prepared to contain glucose at a concentration of 2.0%. Then, batch cultivation was carried out at 47° C. in the same manner as that of Example 1 that will be described later, to produce hydrogen. The amount of the produced hydrogen was measured by the method of Example 1 that will be described later, followed by calculation of the hydrogen yield (mol/mol-monosaccharide) and the maximum hydrogen production rate. Here, the term hydrogen yield refers to a number of moles of hydrogen produced from 1 mol of monosaccharide. Moreover, the maximum hydrogen production rate was expressed by two kinds of denotations: a maximum hydrogen production rate per liter of the culture liquid (mmol/Lh); and a maximum hydrogen production rate per gram of the bacterial dry weight in the culture liquid (mmol/gh).

The obtained hydrogen yield and the maximum hydrogen production rate of the *Clostridium perfringens* strain HN001 were compared with those of known representative hydrogen-producing bacteria. The results of this comparison are shown in Table 4. The hydrogen yield and the like of these bacterial strains except for the strain HN001 are based on the description of Non-patent Document 1. The parts having no description of the corresponding data in the document are left with bars.

TABLE 4

| | Cultivation method | pH | Temp. [° C.] | Substrate | Hydrogen yield [mol/mol] | Hydrogen production rate [mmol/L · h] | [mmol/g · h] |
|---|---|---|---|---|---|---|---|
| *C. perfringens* HN001 | B | 6 | 47 | glucose (2.0%) | 2.4 | 160 | 44 |
| *C. perfringens* HN001 | B | 6 | 47 | glucose (1.5%) | 2.2 | 135 | 37 |
| Bacteria belonging to *Clostridium* | | | | | | | |
| *C. beijerinckii* AM21B | B | — | 41 | glucose | 2 | 24 | 25 |
| *C. paraputrificum* M-21 | B | — | 37 | GlcNAc | 2.5 | 31 | — |
| *C. butyricum* LMG 1213tl | C | 5.8 | 36 | glucose | 1.5 | 22 | — |
| *Clostridium* sp. No 2 | C | 6 | 36 | glucose | 2.4 | 21 | — |
| Bacteria belonging to *Enterobacter* | | | | | | | |
| *E. aerogenes* E.82005 | B | 6 | 38 | glucose | 1 | 21 | 17 |
| *E. cloacae* IIT-BT 08 | B | — | 36 | sucrose | 3 | 35 | 29 |
| *E. aerogenes* E.2005 | C | 6 | 38 | molasses | 0.7 | 36 | 17 |
| *E. aerogenes* HU-101mAY-2 | C | — | 37 | glucose | 1.1 | 58 | — |
| High-temperature bacteria | | | | | | | |
| *Thermotoga maritima* | B | — | 80 | glucose | 4 | 10 | — |
| *Thermotoga elfii* | B | 7.4 | 65 | glucose | 3.3 | 3 | 5 |

TABLE 4-continued

| | Cultivation method | pH | Temp. [° C.] | Substrate | Hydrogen yield [mol/mol] | Hydrogen production rate [mmol/L · h] | [mmol/g · h] |
|---|---|---|---|---|---|---|---|
| *Caldicellulosiruptor saccharolyticus* | B | 7 | 70 | sucrose | 3.3 | 8 | 12 |
| *Clostridium thermocellum* | B | — | 60 | cellobiose | 1 | 7 | 14 |

B: Batch cultivation, C: Continuous cultivation, Unit of hydrogen yield is [mol/mol-monosaccharide].

*Clostridium perfringens* strain HN001 showed a hydrogen yield of 2.4 by batch cultivation at 47° C. and pH 6.0. That is, the bacterial strain was capable of producing 2.4 mol of hydrogen from 1 mol of glucose. In addition, the maximum hydrogen production rate per liter of the culture liquid was 160 mmol/Lh, and the maximum hydrogen production rate per gram of the bacterial dry weight in the culture liquid was 44 mmol/gh.

On the other hand, as for the other bacterial strains described in the table, the highest maximum hydrogen production rate per liter of the culture liquid was 58 mmol/Lh of *Enterobacter aerogenes* HU-101 mAY-2, and the highest maximum hydrogen production rate per gram of the bacterial dry weight in the culture liquid was 29 mmol/Lh of *Enterobacter cloacae* IIT-BT08. Since the comparison was made with reference values obtained under different experimental conditions, no simple comparison could be made. However, it is apparent that *Clostridium perfringens* strain HN001 has a much higher maximum hydrogen production rate than those of other known hydrogen-producing bacteria. Moreover, the hydrogen yield was sufficiently satisfactory. Accordingly, it is apparent that *Clostridium perfringens* strain HN001, that is, the bacterium belonging to the genus *Clostridium* of the present invention excels in hydrogen productivity much better than the other known hydrogen-producing bacteria.

From the abovementioned results, as for the bacterium belonging to the genus *Clostridium* of the present invention, in particular, *Clostridium perfringens*, there is employed a hydrogen-producing bacterium which has a property of producing hydrogen at a rate of 60 mmol or more per hour per liter of a culture liquid which contains glucose as a substrate, by batch cultivation in the YNU anaerobic culture medium at 47° C. and pH 6.0. Furthermore, the hydrogen productivity of the bacterium belonging to the genus *Clostridium* of the present invention preferably achieves a hydrogen production rate of 80 mmol or more, and particularly preferably 100 mmol or more, per hour per liter of the culture liquid. The use of the bacterium belonging to the genus *Clostridium* having a hydrogen productivity within this range enables hydrogen production with higher efficiency than ever before.

In addition, the upper limit of the hydrogen production rate of the bacterium belonging to the genus *Clostridium* of the present invention is not specifically limited as long as it is 60 mmol or more per hour per liter of a culture liquid under the abovementioned cultivation condition, although the hydrogen production rate is preferably higher. The bacteria belonging to the genus *Clostridium* of the present invention acquired by the abovementioned method normally have hydrogen production rates of 60 to 250 mmol under the same condition. Moreover, the preferred range of the hydrogen production rate is 80 to 200 mmol, more preferably 100 to 180 mmol, and most preferably 100 to 160 mmol.

5. Optimum Temperature for Hydrogen Production

The pre-culture liquid was prepared in the same manner as the above-mentioned paragraph 4. Measurement of hydrogen productivity. The pre-culture liquid was added at 8 mL each to 350 mL of the YNU anaerobic culture medium at pH 6.0 or 6.5 in a 500 mL volume flask, followed by batch cultivation at a stirring speed of 30 rpm in the same manner as that of Example 1 that will be described later, to produce hydrogen. The cultivation temperature was set at respectively 41, 44, 47, and 50° C. Moreover, the pH was kept constant by an automatic controller. The amount of the produced hydrogen was measured by the method of Example 1 that will be described later, followed by calculation of the hydrogen yield and the maximum hydrogen production rate per liter of the culture liquid.

TABLE 5

| | Cultivation temperature [° C.] | Hydrogen production rate [mmol/L · h] | Hydrogen yield [mol/mol-glucose] |
|---|---|---|---|
| pH 6.0 | 41 | 59.8 | 1.30 |
| | 44 | 94.2 | 1.93 |
| | 47 | 119.2 | 2.15 |
| | 50 | 111.1 | 2.22 |
| pH 6.5 | 41 | 41.1 | 0.82 |
| | 44 | 71.4 | 1.39 |
| | 47 | 91.1 | 1.42 |
| | 50 | 80.4 | 2.12 |

Glucose concentration: 1.5%

Table 5 shows the hydrogen yields and the maximum hydrogen production rates per liter of the culture liquid at respective cultivation temperatures. The maximum hydrogen production rate showed the lowest values at 41° C. for both pH 6.0 and pH 6.5, which were respectively 59.8 mmol/Lh and 41.1 mmol/Lh. These values are lower than the maximum hydrogen production rates at other cultivation temperatures, but are sufficiently satisfactory maximum hydrogen production rates as is apparent from a comparison with Table 4. Accordingly, it is apparent that *Clostridium perfringens* strain HN001 is capable of satisfactorily producing hydrogen at 47 to 50° C.

In addition, as is apparent from Table 5, the maximum hydrogen production rate was highest at 47° C. for both pH 6.0 and pH 6.5, and the hydrogen yield was highest at 50° C. for both pH 6.0 and pH 6.5. That is to say, it is apparent that the most suitable temperature for the hydrogen production of *Clostridium perfringens* strain HN001, that is, the bacterium belonging to the genus *Clostridium* of the present invention is 47° C. to 50° C. In addition, since the optimum temperature for the growth is 44 to 47° C., the growth rate was found to be not necessarily proportional to the hydrogen production rate.

The bacterium belonging to the genus *Clostridium* of the present invention was acquired from bacteria which have originally been residing in liquids and sludges collected from sewage and the like, namely biomass, through selection of a bacterium which excels in hydrogen productivity, in particular, hydrogen production rate. Accordingly, the bacterium belonging to the genus *Clostridium* of the present invention is capable of producing a large amount of hydrogen with higher efficiency than ever before, even from biomass as a production source.

The bacterium belonging to the genus *Clostridium* of the present invention can be cultured by a usual method for use in the cultivation of bacteria belonging to the genus *Clostridium*, and anaerobic cultivation is preferred. Either batch cultivation or continuous cultivation may be employed. Since the risk of contamination can be reduced and no special devices are needed, batch cultivation is preferred for the production of a small amount of hydrogen. On the other hand, since the cultivation condition can be readily kept constant and the productivity can be stabilized, continuous cultivation is preferred for the production of a large amount of hydrogen such as industrial production. When performing continuous cultivation, the bacterium belonging to the genus *Clostridium* of the present invention may also be immobilized to a usual carrier.

The culture liquid for use in the cultivation of the bacterium belonging to the genus *Clostridium* of the present invention is not specifically limited, and usual culture liquids for use in cultivation of bacteria belonging to the genus *Clostridium* including commercially available media for anaerobes can be used. Examples of these media include the ABCM semisolid medium and the YNU anaerobic culture medium. The glucose concentration of the culture liquid can be appropriately determined according to the cultivation condition or the like. In addition, the cultivation temperature is not specifically limited as long as the bacterium belonging to the genus *Clostridium* of the present invention can grow, although preferred is 44 to 47° C.

Efficient hydrogen production can be achieved by cultivation of the bacterium belonging to the genus *Clostridium* of the present invention by a usual method. The culture liquid for the hydrogen production is not specifically limited as long as it is a usual culture liquid for use in cultivation of bacteria belonging to the genus *Clostridium*, although the YNU anaerobic culture medium is preferred. In addition, a food waste such as raw garbage and other industrial wastes may also be used as the raw material of the culture liquid for the bacterium belonging to the genus *Clostridium* of the present invention as long as the effect of the present invention is not impaired. Even from such a raw material, the bacterium belonging to the genus *Clostridium* of the present invention can enable hydrogen production with higher efficiency than ever before.

In addition, the cultivation temperature for the hydrogen production is preferably 47 to 50° C. from the viewpoint of hydrogen production efficiency. Moreover, the pH of the culture liquid for the hydrogen production is not specifically limited, although it is preferably 5.8 to 6.5, and particularly preferably 6.0 to 6.2.

Moreover, the sugar component contained in the culture liquid or the food wastes etc. as the fermentation medium for the hydrogen production is not specifically limited as long as it can serve as the substrate for the hydrogen fermentation of the bacterium belonging to the genus *Clostridium* of the present invention. Examples thereof can include monosaccharides such as glucose, maltose, and sucrose, and polysaccharides such as starch. The concentration of such components serving as the substrate for the hydrogen fermentation can be appropriately determined according to the cultivation condition or the like, although it is preferably 0.5 to 5% by weight, and more preferably 1.5 to 2.5% by weight in the culture liquid.

Furthermore, other cultivation conditions for the hydrogen production are not specifically limited as long as the effect of the present invention is not impaired. However, the bacterium belonging to the genus *Clostridium* of the present invention is preferably cultured at a hydrogen production rate within a range of 60 to 250 mmol/L·h, preferably 80 to 200 mmol/L·h, and more preferably 100 to 180 mmol/L·h, as well as the abovementioned conditions of the cultivation temperature, the culture liquid, and the like.

Next is a more detailed description of the present invention with examples. However, the present invention is in no way limited to the following examples.

EXAMPLE 1

*Clostridium perfringens* strain HN001 was inoculated in a test tube containing 16 n L of the ABCM semisolid stab culture medium, and was subjected to anaerobic cultivation at 30° C. for 16 hours. Then, in order to acclimatize to high temperatures, the test tube was anaerobically incubated at 45° C. for 30 minutes for use as a pre-culture liquid. The pre-culture liquid was added at 8 mL each to 350 mL of the YNU anaerobic culture medium at pH 6.0 in a 500 mL jar fermenter, followed by batch cultivation at a stirring speed of 30 rpm. The cultivation temperature was set at 32, 37, 41, 44, 47, and 50° C., respectively. Moreover, the pH was kept constant by an automatic controller.

The produced hydrogen gas was collected in a measuring cylinder and quantified by the liquid displacement method using 10% sodium hydroxide aqueous solution to remove carbon dioxide. The thus collected gas was confirmed to be hydrogen gas through analysis using gas chromatography. The amount of the produced amount was used to calculate the hydrogen yield and the maximum hydrogen production rate per liter of the culture liquid.

Figure 2A:
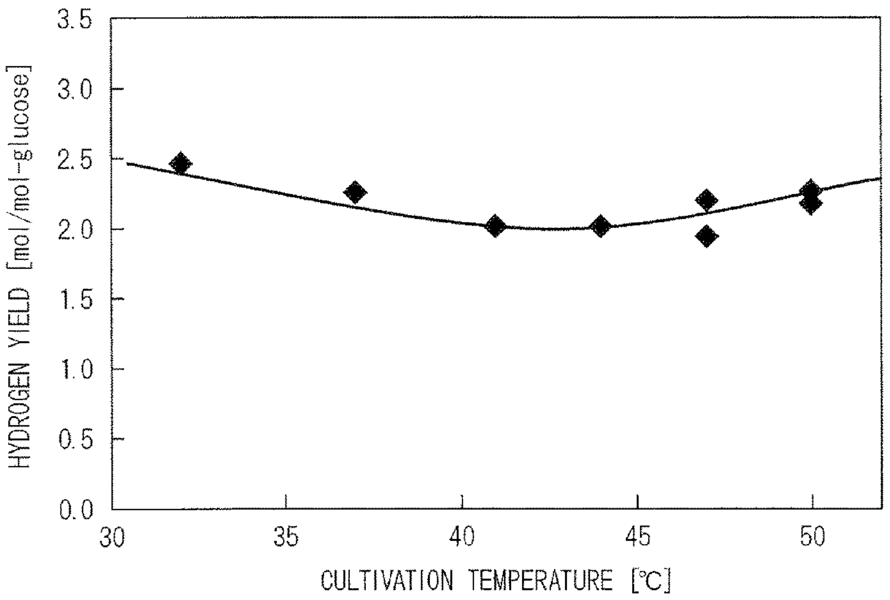
FIG. 2A shows the hydrogen yields at respective temperatures in Example 1.
Figure 2B:
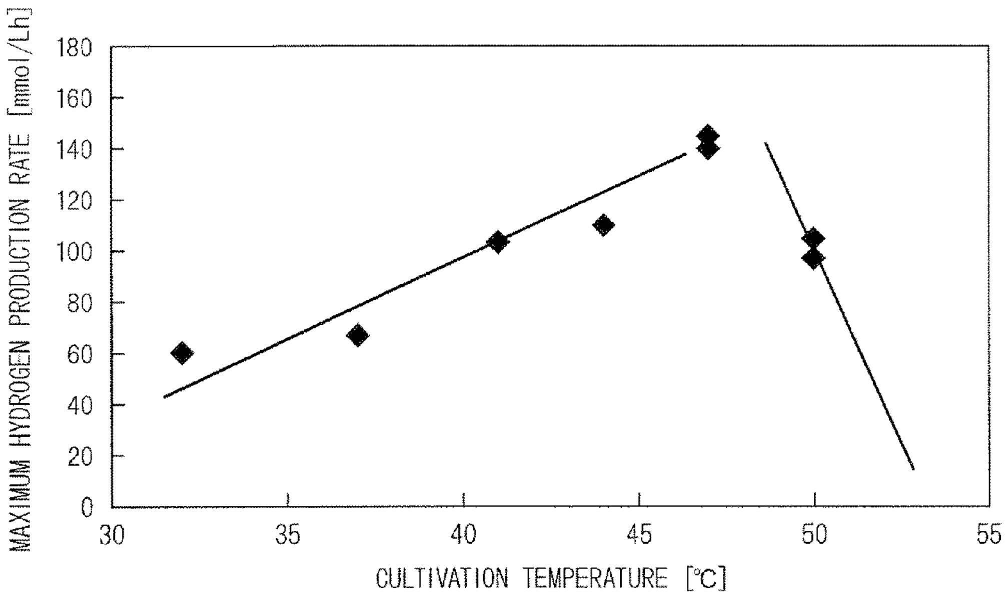
FIG. 2B shows the maximum hydrogen production rates per liter of the culture liquid at respective temperatures.

FIG. 2A shows the hydrogen yields at the respective cultivation temperatures and FIG. 2B shows the maximum hydrogen production rates per liter of the culture liquid at the respective cultivation temperatures. The maximum hydrogen production rate at 47° C. was about 135 mmol/Lh. In addition, the maximum hydrogen production rate was highest at 47° C., while the hydrogen yield was found to be prone to increase at about 32° C. and 50° C.

From the results of Example 1, it is apparent that *Clostridium perfringens* strain HN001, that is, the bacterium belonging to the genus *Clostridium* of the present invention is capable of producing hydrogen at a rate of 60 mmol or more per hour per liter of a culture liquid which contains glucose as a substrate, by batch cultivation in the YNU anaerobic culture medium at 47° C. and pH 6.0, and the most suitable cultivation temperature for the hydrogen production is 47° C. to 50° C.

EXAMPLE 2

The amount of hydrogen produced from each culture was measured in the same manner as that of Example 1, except that the pH of the YNU anaerobic culture medium was set at 5.5, 6.0, 6.5, and 7.0, and the cultivation temperature was set at 47° C. only. Then, the hydrogen yield and the maximum hydrogen production rate per liter of the culture liquid were calculated.

TABLE 6

| pH for cultivation | Hydrogen production rate [mmol/L · h] | Hydrogen yield [mol/mol-glucose] |
|---|---|---|
| 5.5 | 33.9 | 1.96 |
| 6.0 | 111.2 | 2.22 |
| 6.5 | 80.4 | 2.12 |
| 7.0 | 38.4 | 1.29 |

Glucose concentration: 1.5%

Table 6 shows the hydrogen yields and the maximum hydrogen production rates per liter of the culture liquid at respective pH values. The hydrogen yield and the maximum hydrogen production rate were both highest at 6.0. The maximum hydrogen production rate at pH 6.5 was 80.4 mmol/Lh which greatly exceeded 60 mmol/1 Therefore it is apparent that the pH of the culture liquid for the hydrogen production is preferably 5.8 to 6.5, and particularly preferably 6.0 to 6.2.

INDUSTRIAL APPLICABILITY

The bacterium belonging to the genus *Clostridium* of the present invention excels in hydrogen productivity, and thus is usable in the field of hydrogen production from biomass as a production source.

The invention claimed is:

1. An isolated bacterium *Clostridium perfringens*, which has a property of producing hydrogen at a rate of 60 mmol or more per hour per liter of a culture liquid which contains glucose as a substrate, by batch cultivation in a YNU anaerobic culture medium at 47° C. and pH 6.0, wherein the bacterial strain is *Clostridium perfringens* HN001 (NITE BP-318).

2. An isolated bacterium *Clostridium perfingens*, according to claim 1, wherein the optimum temperature for hydrogen production is 47 to 50° C.

3. An isolated bacterium *Clostridium perfringens*, according to claim 1, wherein the optimum temperature for cell growth is 44 to 47° C.

4. An isolated bacterium *Clostridium perfringens*, according to claim 1, wherein the bacterium has a raffinose-decomposing ability.

5. A method of producing hydrogen comprising: anaerobically incubating the isolated bacterium *Clostridium perfringens* according to claim 1 at a pH of 6.0 to 6.5 and at a temperature of 45 to 50° C.

6. A method of producing hydrogen according to claim 5, wherein the temperature is 47 to 50° C.

* * * * *